US008586821B2

(12) United States Patent
Wang et al.

(10) Patent No.: US 8,586,821 B2
(45) Date of Patent: Nov. 19, 2013

(54) MELT-PROCESSED FILMS OF THERMOPLASTIC CELLULOSE AND MICROBIAL ALIPHATIC POLYESTER

(75) Inventors: James H. Wang, Appleton, WI (US); JaeHong Lee, Yongin-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 742 days.

(21) Appl. No.: 12/645,861

(22) Filed: Dec. 23, 2009

(65) Prior Publication Data

US 2011/0152818 A1 Jun. 23, 2011

(51) Int. Cl.
*A61F 13/514* (2006.01)
(52) U.S. Cl.
USPC .......................... 604/370; 604/374
(58) Field of Classification Search
USPC ........................ 604/385.23, 385.01
See application file for complete search history.

(56) References Cited

U.S. PATENT DOCUMENTS

| | | | |
|---|---|---|---|
| 3,194,776 A * | 7/1965 | Caldwell | 524/311 |
| 4,069,822 A * | 1/1978 | Buell | 604/366 |
| 5,217,803 A | 6/1993 | McBride et al. | |
| 5,254,607 A | 10/1993 | McBride et al. | |
| 5,256,711 A | 10/1993 | Tokiwa et al. | |
| 5,281,691 A * | 1/1994 | Hubbs et al. | 528/361 |
| 5,292,783 A | 3/1994 | Buchanan et al. | |
| 5,417,679 A | 5/1995 | Toms et al. | |
| 5,625,029 A | 4/1997 | Hubbs et al. | |
| 5,714,230 A | 2/1998 | Kameoka et al. | |
| 5,939,467 A * | 8/1999 | Wnuk et al. | 523/128 |
| 6,096,809 A | 8/2000 | Lorcks et al. | |
| 6,506,824 B1 | 1/2003 | Bastioli et al. | |
| 6,933,335 B1 | 8/2005 | Berger et al. | |
| 7,176,251 B1 | 2/2007 | Bastioli et al. | |
| 2001/0039303 A1 | 11/2001 | Loercks et al. | |
| 2003/0108701 A1* | 6/2003 | Bond et al. | 428/35.7 |
| 2004/0009268 A1 | 1/2004 | Axelrod et al. | |
| 2004/0014883 A1* | 1/2004 | Yamamoto et al. | 524/599 |
| 2008/0082069 A1 | 4/2008 | Qin et al. | |
| 2008/0147034 A1 | 6/2008 | Wang et al. | |
| 2008/0188593 A1 | 8/2008 | Bastioli et al. | |

FOREIGN PATENT DOCUMENTS

WO WO 95/15260 A1 6/1995
WO WO 97/34953 A1 9/1997

* cited by examiner

*Primary Examiner* — Susan Su
(74) *Attorney, Agent, or Firm* — Randall W. Fieldhack; Kenya T. Pierre; Denise L. Stoker (57) ABSTRACT

Films made from a thermoplastic cellulose and microbially-derived, renewable and biodegradable aliphatic polyester such as polyhydroxyalkanoates are disclosed. The films, made from two relatively brittle materials exhibit more ductility and strength than the materials from which the film is made. The film may be incorporated into absorbent personal care product including but not limited to training pants, diaper, bandages, and bed pads.

9 Claims, 9 Drawing Sheets

MELT-PROCESSED FILMS OF THERMOPLASTIC CELLULOSE AND MICROBIAL ALIPHATIC POLYESTER

BACKGROUND

The present invention relates to a thermoplastic article. In particular, the invention pertains to a melt-processed thermoplastic film that contains a thermoplastic cellulose and a microbially-derived, renewable and biodegradable aliphatic polyester. The composition may be incorporated into a variety of products.

Because of increasing consumers' concern on environmental issues and the alleged depletion of fossil fuels, using environmentally sustainable materials in consumer products has attracted increased attention in recent decades. From an environmental sustainability standpoint, cellulose material is an attractive natural material made from abundant renewable sources ranging from wood to agricultural waste.

It is known that some cellulose derivatives can be thermally processed into various articles such as film and molded articles. However, the short carbon chain alkanoates derivatives of cellulose such as cellulose acetate and cellulose propionate have high melting temperatures making them not suitable for blending with microbial aliphatic polyester such as poly(3-hydroxybutyrate) due to its thermal decomposition at processing temperatures.

In recent years, manufacturers of plastic or thermoplastic products or materials have shown increasing interest in renewable biopolymers and cellulose-based materials as important, environmentally-friendly, natural resources. In fact, cellulose-based materials are the most abundant natural polymers that can be renewably produced each year in large quantities.

Commercially available thermoplastic cellulose derivatives are cellulose esters and ethers such as cellulose acetate (CA), cellulose acetate propionate (CAP), and cellulose acetate butyrate (CAB), methyl cellulose, ethyl cellulose, hydroxypropyl cellulose, etc. Common properties of these cellulose derivatives are that they tend to have high stiffness, low ductility, good clarity, and a narrow thermal processing window. They also have moderate heat and impact resistance. Unfortunately, the rigid and brittle nature of cellulose derivatives tends to limit their wider use in a variety of products and applications.

Native cellulose is not thermoplastic. Most cellulose esters have high melting temperatures of over 230 to 240° C. or higher, while poly(3-hydroxybutyrate) (PHB) has a melting point of 177° C. and a thermal decomposition temperature of about 200° C. Therefore most cellulose esters, even some cellulose acetate butyrate compositions having high melting points, cannot be melt blended with PHB due to decomposition of the polyhydroxyalkanoate (PHA).

To improve the performance of cellulose ester materials, blending cellulose derivatives with other polymers has been explored. The prior art blends of cellulose ester with biodegradable polymers are prepared by solution blending. Solution prepared films typically have different morphology and properties from the films of the same composition produced by melt processing. This is because melt processing cannot achieve the molecular level mixing that can be achieved in a solution blending process. However, the solution blending method is not preferred due to the use and recovery of solvents as well the corresponding environmental impact.

Thus, there is a need for environmentally sustainable films made from 100% renewable polymers. There is also a need for renewable polymers such as cellulose for sustainable plastic applications in personal hygiene and health care products. There is a further need for a film composition of cellulose and PHA with suitable melting temperatures and stability during melt processing without causing PHA to decompose. There is yet another need for melt-processed films that have suitable mechanical properties such as enhanced flexibility and ductility.

SUMMARY

The present invention discloses a new thermoplastic film that exhibits synergistic properties. Typically, when two rigid materials are combined, one would expect that the new material would exhibit the physical attributes between the original two materials, i.e. following an additivity type linear relationship of the component polymers. In stark contrast, by the present invention, it was unexpected to find that the blending of particular percentages of two usually rigid or non-ductile polymers can generate a rather ductile film material.

In one aspect of the present invention is a melt-processed thermoplastic material film made from a blend of about 5% to about 95% of a thermoplastic cellulose having a melting point temperature between about 100° C. to about 200° C., and about 5 wt. % to about 95 wt. % of a polyhydroxyalkanoates with an average molecular weight of at least 20,000 g/mol.

In another aspect of the present invention is an absorbent article made with a backsheet comprising the film of a melt processed thermoplastic material; a top sheet attached to the backsheet, and an absorbent core disposed between the backsheet and topsheet, and directly attached to either the backsheet or the topsheet.

In yet another aspect of this invention is a packaging film or article comprising the film of this invention. The packaging article includes product bags, molded containers, bottles, etc.

DETAILED DESCRIPTION

Blend compositions used herein are by weight percent of the composition unless otherwise stated.

Both cellulose esters and PHB are highly rigid and brittle polymers. By blending these two polymer compositions together in a melting process, it was unexpected to find that the film made from the two rigid polymers has reduced rigidity and increased ductility. The film also has great clarity, whereas films made from microbial aliphatic polyester are usually opaque. The blend of the present invention is stable at melting temperatures to allow for thermoplastic processing.

The films of the present invention have at least two renewable and biodegradable components: 1) plasticized cellulose derivative (desirably a non-food-based material) and 2) a biodegradable and renewable polymer such as polyhydroxyalkanoate (PHA), e.g. poly(3-hydroxybutyrate) (PHB). Thermoplastic blend films of this invention are flexible and have a relatively high tensile strength. These properties are desirable for disposable absorbent product applications.

It is known that cellulose derivatives; such as cellulose acetate, cellulose acetate propionate, and cellulose acetate butyrate, etc.; can be thermally processed into various articles such as film, molded articles. However, the short carbon chain cellulose alkanoates derivatives such as cellulose acetate and cellulose propionate have high melting temperatures making them not suitable for blending with PHA.

Native cellulose cannot be thermoplastically processed due to the fact that cellulose has a decomposition temperature lower than the melting temperature. Modification of the native cellulose makes it possible to use in thermoplastic applications. Commercially available thermoplastic cellulose derivatives are cellulose esters and ethers such as cellulose acetate (CA), cellulose acetate propionate (CAP), cellulose butyrate, and cellulose acetate butyrate (CAB), methyl cellulose, ethyl cellulose, hydroxypropyl cellulose, etc. The thermoplastic cellulose may include an alkyl cellulose and hydroxyalkyl cellulose with 1 to 10 carbon in an alkyl or hydroxyalkyl groups. In another embodiment, the thermoplastic cellulose may include cellulose alkanoate with 2 to 10 carbon in an alkanoate group. In yet another embodiment, the thermoplastic cellulose may include cellulose alkanoate with two or more different alkanoate groups. In a further embodiment, the thermoplastic cellulose comprises alkyl cellulose and hydroxyalkyl cellulose with 1 to 10 carbon in an alkyl or hydroxyalkyl group. In another embodiment, the thermoplastic cellulose may include methyl cellulose, ethyl cellulose, methyl propyl cellulose, hydroxyethyl cellulose, hydroxypropyl cellulose, and/or hydroxybutyl cellulose. In another embodiment, the thermoplastic cellulose includes alkyl cellulose and hydroxyalkyl cellulose.

The common properties of these native cellulose derivatives include high stiffness, high tensile strength, low ductility, good clarity, and narrow thermal processing window. They also have moderate heat and impact resistance. The rigid and brittle nature of these cellulose derivatives makes it appropriate for number of limited applications. To improve the performance, the cellulose derivatives are blended with other polymers according to the present invention.

Not all CAB materials are suitable for this invention. There are several criteria for selecting CAB for making the film of the present invention: 1) the composition of CAB or thermoplastic cellulose has a melting point from 100° C. to about 200° C.; 2) the composition of CAB has a butyrate to acetate weight ratio of 1 or greater; 3) butyrate content in CAB is desirably 30% or greater; 4) the molecular weight of CAB is at least 20,000 g/mol. Higher molecular weight analog such as alkanoates with five or more carbon are also suitable for this invention. Typically as the number of carbon in the alkanoate of cellulose derivative increases, the melting temperature of the cellulose derivative decreases.

In one aspect, the desirable thermoplastic cellulose derivative, cellulose acetate butyrate (CAB), (grade: Tenite butyrate 485-10, plasticizer: 10% of bis(2-ethylhexyl) adipate, composition: 37 wt % of butyrate, 13.5 wt % of acetate, DS (degree of substitution): 2.4~2.8, purchased from Eastman (Minneapolis, Minn.), was used for creating examples listed in this invention disclosure.

The average molecular weight of polyhydroxyalkanoate (PHA) is desirably at least 20,000 g/mol. Short chain or medium chain PHAs such as poly(3-hydroxybutyrate) (PHB), poly(3-hydroxybutyrate-co-3-hydroxyvalerate) (PHBV), poly(3-hydroxybutyrate-co-4-hydroxybutyrate (P3HB-4HB), poly(3-hydroxybutyrate-co-3-hydroxyhexanoate) (PHB-Hx), poly(3-hydroxybutyrate-3-hydroxyoctanoate (P3HB-O), etc. can be utilized in some aspects of this invention.

One particular example of PHA is PHB: Polyhydroxybutyrate (PHB) is an isotactic, linear, thermoplastic aliphatic homopolyester 3-hydroxy butyric acid. PHB is water-insoluble and highly crystalline (60 to 70%), providing excellent resistance to solvents. In one aspect, PHB, namely BIOMER P226, may be purchased from Biomer Ltd. (Germany).

EXAMPLE 1

The films of this embodiment of the present invention were made on a THERMO PRISM USALAB 16 twin screw extruder (Thermo Electron Corp., Stone, England). The melt blending and film extrusion were made in the same process, e.g. a direct extrusion and cast film extrusion process. The extruder had 11 heating zones, numbered consecutively 1-10 from the feed hopper to the die. 100% CAB was initially added to a feeder that delivers the material into the feedthroat of the extruder. The first barrel received the CAB at a rate of 1 lb/hr. The temperature profile of zones 1 through 10 of the extruder was 175~195° C. for each zone (exact temperatures are listed in Table 1). The die temperature was 180° C. The screw speed was set at 15 rpm and the torque during extrusion process was 70~75%. Film casting was conducted directly by attaching a 4″ film die on the extruder. The extruded film from the 4″ die was cooled on the chill-roll of a film take-up device.

The CAB film of the present invention was clear and had no unmelted particles or other impurities.

EXAMPLES 2-6

The melt blending and film casting of a CAB and PHB blend was conducted in the manner described above in Example 1. The temperature profile of zones and operating conditions are listed in Table 1. All polymers were dry blended and the fed to an extruder. Film casting was conducted directly by attaching a 4″ film die on the extruder. The screw speed ranged from 15 to 22 rpm. The torque during the film extrusion experiments for Examples 2 to 6 ranged from 28 to 64%.

Typically, as processing temperatures are reduced, the melt pressure and torque tend to increase due to increased melt viscosity. However, the process of melt blending according to the present invention yielded unexpected results. First, it is shown that it is possible to substantially reduce the melt processing temperatures of CAB by blending it with PHB. The die temperature was reduced from 190° C. to 170° C. This reduces the energy requirements for processing CAB. For instance, see Examples 2 and 6 as compared to Example 4. For a further energy savings, the torque was also reduced with the addition of PHB in the composition.

EXAMPLE 7

A film having 100% PHB is made in the manner described above in Example 1. The first barrel received PHB at a rate of 1.5 lbs/hr. The temperature profile of zone 1 to 10 of the extruder was 155~165° C. for each zone, as seen in Table 1. The die temperature was 165° C. The screw speed was set at 22 rpm and the torque during extrusion process was 62~65%. The extrusion process and film casting were successfully performed.

TABLE 1

Blending and Film Casting Condition for Thermoplastic CAB and PHB

| Sample No. | CAB/PHB ratio | Mixture feeding rate (lb/hr) | Extruder speed (rpm) | T1 | T2 | T3 | T4 | T5 | T6 | T7 | T8 | T9 | Adaptor | Die | $P_{melt}$ psi | Torque (%) |
|---|---|---|---|---|---|---|---|---|---|---|---|---|---|---|---|---|
| Example 1 | 100/0 | 1 | 15 | 175 | 175 | 180 | 180 | 185 | 185 | 195 | 195 | 195 | 195 | 180 | 25-30 | 70~75 |
| Example 2 | 80/20 | 1 | 15 | 165 | 170 | 170 | 170 | 175 | 175 | 180 | 180 | 180 | 180 | 180 | 18~20 | 34~36 |
| Example 3 | 70/30 | 1 | 15 | 165 | 170 | 170 | 170 | 175 | 175 | 180 | 180 | 180 | 180 | 180 | 14~15 | 30~32 |
| Example 4 | 50/50 | 1.2 | 20 | 165 | 170 | 170 | 170 | 175 | 175 | 180 | 180 | 180 | 180 | 180 | 12~15 | 28~32 |
| Example 5 | 30/70 | 1.5 | 20 | 160 | 165 | 165 | 165 | 170 | 170 | 170 | 175 | 175 | 175 | 180 | 9~10 | 35~38 |
| Example 6 | 20/80 | 1.5 | 20 | 155 | 155 | 155 | 155 | 160 | 160 | 160 | 165 | 165 | 170 | 170 | 9~10 | 60-64 |
| Example 7 | 0/100 | 1.5 | 22 | 155 | 155 | 155 | 155 | 160 | 160 | 160 | 165 | 165 | 165 | 165 | 8~10 | 62~65 |

Tensile Strength: The tensile strength of the films of the present invention was tested according the "Standard Test Method for Tensile Properties of Plastics," ASTM 938-99, published by the American Society of Testing and Materials. The tensile properties of the exemplary films made from the CAB/PHB blends are shown below in Table 2.

The tensile tests may be performed on a SINTECH1/D with five repetitions in both the machine direction (MD) and the cross direction (CD). Each film sample is cut into a dog-bone shape with a center width of 3.0 mm. The gauge length is 18.0 mm. During the test, samples are stretched at a crosshead speed of 12.7 cm (5.0 inches) per minute until breakage occurs. In one example, the computer program TESTWORKS 4 collected data during the test and generated a stress (MPa) versus strain (%) curve from which a variety of properties can be determined: e.g., modulus, peak stress and elongation.

The blending of CAB and PHB showed a synergistic effect of increasing film ductility. For example, the elongation at break of blending film was greater than that of pure CAB and pure PHB films. Especially, the elongation at break also was increased substantially in MD direction from about 3% for pure PHB to about 98% in Example 4. The improvement in the film's elongation or ductility was unexpected since both the pure CAB and PHB films are brittle materials.

TABLE 2

Tensile Properties of Films

| Example No. | Sample Description | Composition | Film Thickness (mil.) MD | Film Thickness (mil.) CD | Modulus(Mpa) MD | Modulus(Mpa) CD | Peak Stress(Mpa) MD | Peak Stress(Mpa) CD | Elongation (%) MD | Elongation (%) CD |
|---|---|---|---|---|---|---|---|---|---|---|
| Example 1 | CAB/PHB | 100/0 | 1.9 | 1.8 | 1800 | 1100 | 82 | 33 | 13 | 38 |
| Example 2 | | 80/20 | 1.8 | 2.0 | 1200 | 910 | 63 | 31 | 24 | 82 |
| Example 3 | | 70/30 | 1.9 | 1.8 | 600 | 540 | 33 | 26 | 56 | 100 |
| Example 4 | | 50/50 | 2.2 | 2.2 | 120 | 85 | 16 | 14 | 98 | 110 |
| Example 5 | | 30/70 | 1.9 | 2.1 | 1100 | 1000 | 35 | 31 | 35 | 37 |
| Example 6 | | 20/80 | 3.9 | 3.9 | 1000 | 1000 | 30 | 28 | 30 | 19 |
| Example 7 | | 0/100 | 3.5 | 3.5 | 1100 | 540 | 21 | 14 | 3 | 2 |

It was surprising to find that a low modulus of 120 MPa and 85 MPa respectively for MD and CD at PHB/CAB of 50/50 (Example 4). At the 50/50 ratio, the modulus reached a minimum, while the elongation at break reached a maximum (98% and 110% in MD and CD respectively)

Scanning Electron Microscopy (SEM) Examination of CAB/PHB Blend Films:

Machine direction sections were prepared by fracturing the films in the MD direction after chilling the film samples to a cryogenic temperature in liquid nitrogen. The cross direction sections were prepared by cutting the film in the cross-direction using a cryogenically chilled SUPER-KEEN razor while the sample was maintained at cryogenic temperature. The sections were mounted vertically and sputter coated with gold using light burst applications at low current to significantly reduce any possibility of sample heating.

For further evaluation of the film morphologic features, additional sections were prepared and subjected to oxygen plasma etching using an Emitech Inc. K1050X plasma etching unit. Three 4-minute treatments at 50 watts were performed. This regimen was sufficient to provide etching without any evidence of melting. Generally, different polymers are removed at different rates, revealing further structural details in a blend. This process was done for this sample to more clearly confirm the nature of two polymers on the SEM images.

All samples were examined using a JEOL 6490LV scanning electron microscope (SEM) operated at low voltage.

Figure 1:
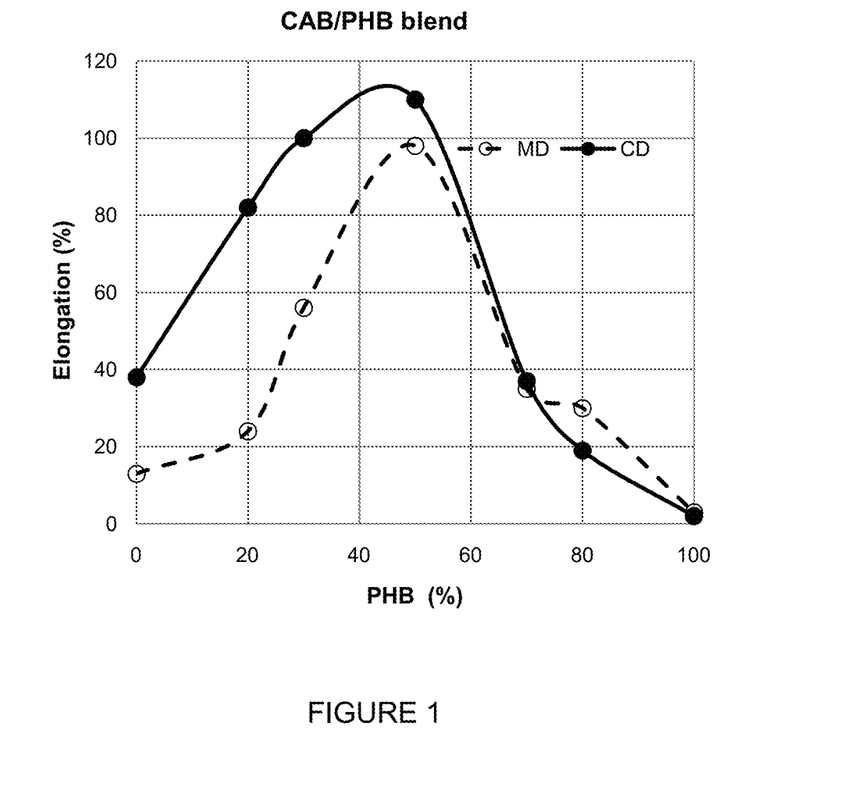
FIG. 1 shows a graph that plots the elongation at break of a polymer blend film as a function of the weight percentage of PHB in the blend.
Figure 2A:
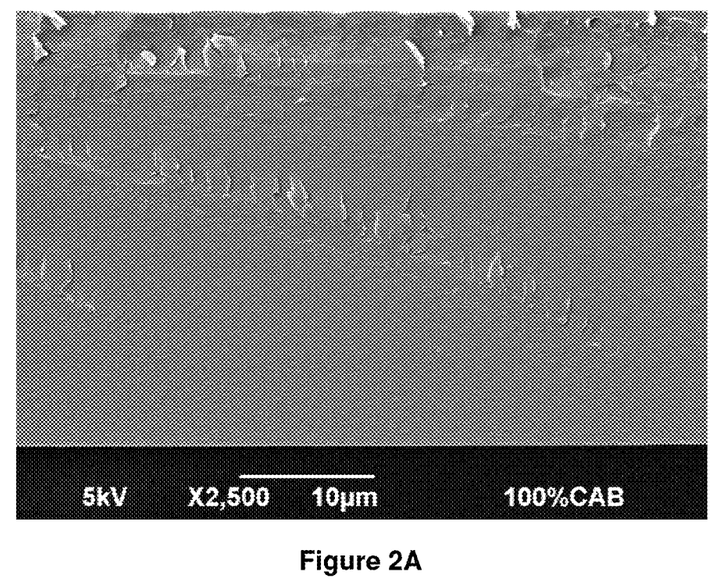
FIG. 2A is a scanning electron microscope (SEM) image of a cross-section of a sheet of pure CAB film, oriented parallel to a machine direction (MD) of the film at 2500× magnification.

FIG. 2A is a SEM image of a cross-section of a sheet of pure CAB film, oriented parallel to a machine direction (MD) of the film at 2500× magnification. This micrograph shows that CAB exhibits glassy brittle-fracture type morphology.

Figure 2B:
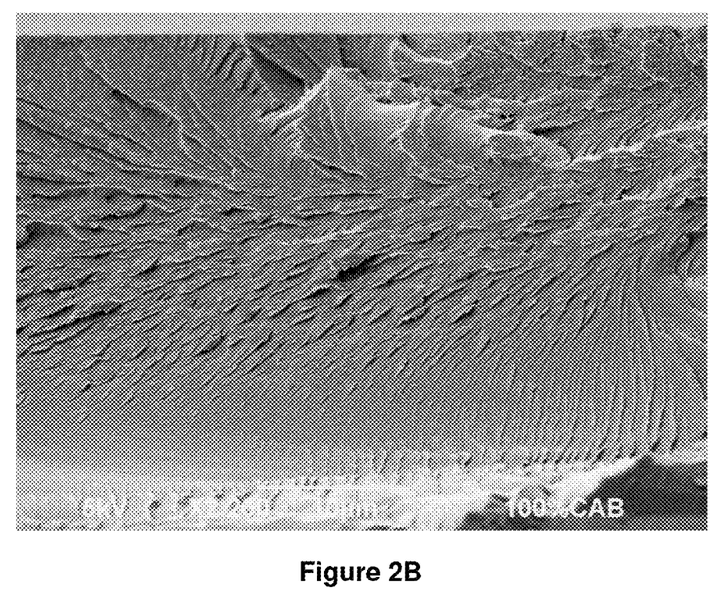
FIG. 2B is a SEM image of a cross-section of the sheet of pure CAB film in FIG. 2A, oriented parallel to a cross-machine direction (CD) of the film at 2200× magnification.

FIG. 2B is a SEM image of a cross-section of the sheet of pure CAB film in FIG. 2A, oriented parallel to a cross-machine direction (CD) of the film at 2200× magnification. This micrograph shows that CAB also exhibits glassy brittle-fracture type morphology.

Figure 3A:
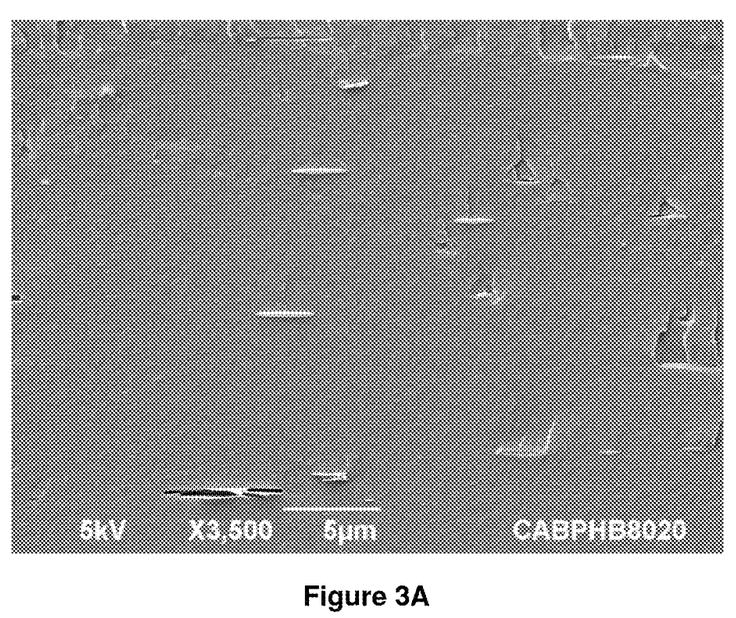
FIG. 3A is a SEM image of a cross-section of a sheet of CAB/PHB blend (80%/20%) film, oriented parallel to its MD at 3500× magnification.

FIG. 3A is a SEM image of a cross-section of a sheet of a CAB/PHB blend (80%/20%) film, oriented parallel to its machine direction at 3500× magnification.

This micrograph shows that CAB forms a continuous glassy fracture phase and PHB forms an elongated dispersed phase.

Figure 3B:
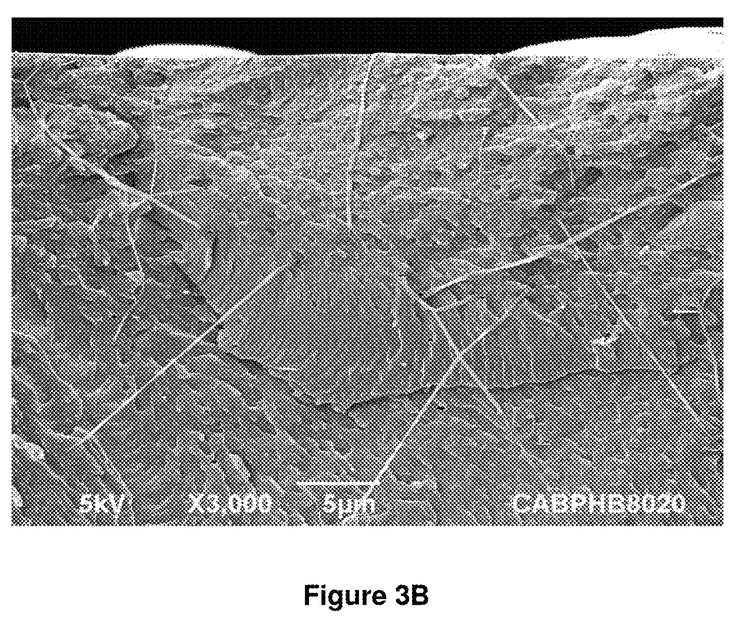
FIG. 3B is a SEM image of a cross-section of the sheet of CAB/PHB blend (80%/20%) film in FIG. 3A, oriented parallel to its CD at 3000× magnification.

FIG. 3B is a SEM image of a cross-section of the sheet of a CAB/PHB blend (80%/20%) film in FIG. 3A, oriented parallel to the sheet cross-direction at 3000× magnification. This micrograph shows that PHB forms a dispersed phase with long, sub-micron diameter filaments. The fracture surface image has shown that the PHB dispersed phase had a ductile elongation since the PHB filament was stretched extensively without breakage, this is quite unexpected based on the brittle nature of pure PHB. The melt processing of the thermoplastic films of this invention may have produced the unique ductile deformation of the blends due to the unique microstructure.

Figure 4A:
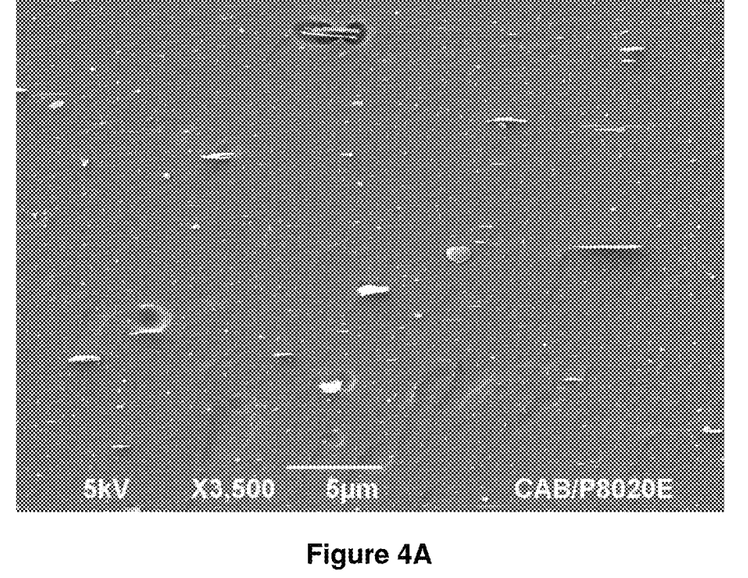
FIG. 4A is a SEM image of a cross-section of a sheet of CAB/PHB blend (80%/20%) film after oxygen plasma etching, oriented parallel to its MD at 3500× magnification.

FIG. 4A is a SEM image of a cross-section of a sheet of a CAB/PHB blend (80%/20%) film after oxygen plasma etching, oriented parallel to the machine-direction at 3500× magnification. This micrograph shows that CAB is the continuous phase, it still exhibits glassy fracture, plasma etching did not have much effect on CAB continuous phase.

Figure 4B:
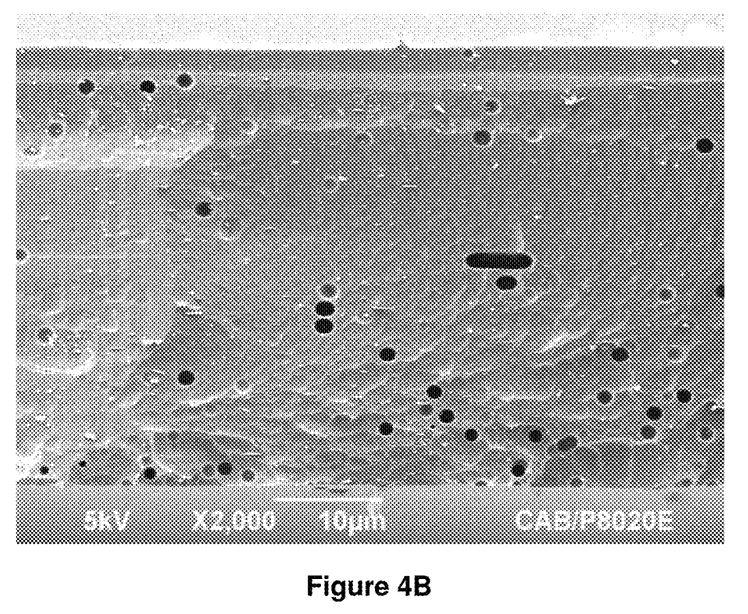
FIG. 4B is a SEM image of a cross-section of the sheet of CAB/PHB blend (80%/20%) film after oxygen plasma etching in FIG. 4A, oriented parallel to its CD at 2000× magnification.

FIG. 4B is a SEM image of a cross-section of the sheet of a CAB/PHB blend (80%/20%) film after oxygen plasma etching in FIG. 4A, oriented parallel to the cross-direction at 2000× magnification. This micrograph shows that voids were formed where PHB filament were etched out, conforming the microfilament structure of PHB in the blends.

Figure 5A:
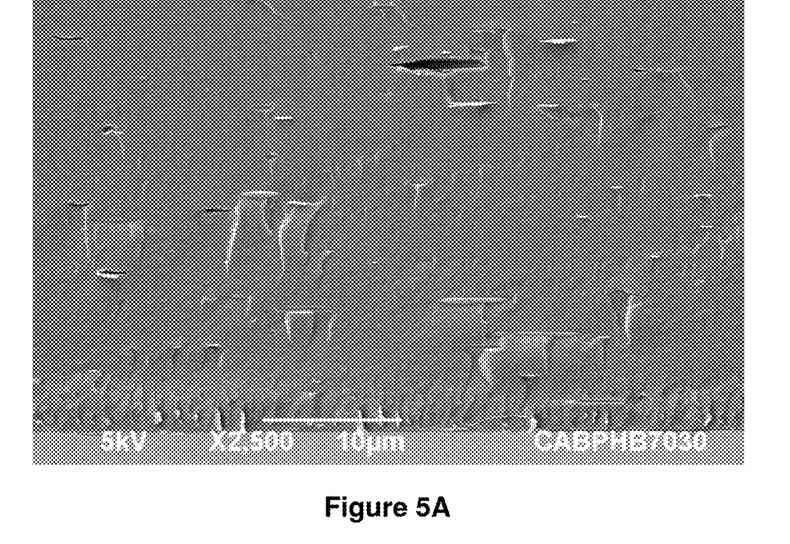
FIG. 5A is a SEM image of a cross-section of a sheet of CAB/PHB blend (70%/30%) film, oriented parallel to its MD at 2500× magnification.

FIG. 5A is a SEM image of a cross-section of a sheet of CAB/PHB blend (70%/30%) film oriented parallel to the machine-direction at 2500× magnification. This micrograph shows that CAB still exhibits glassy fracture surface and PHB filament intersections visible.

Figure 5B:
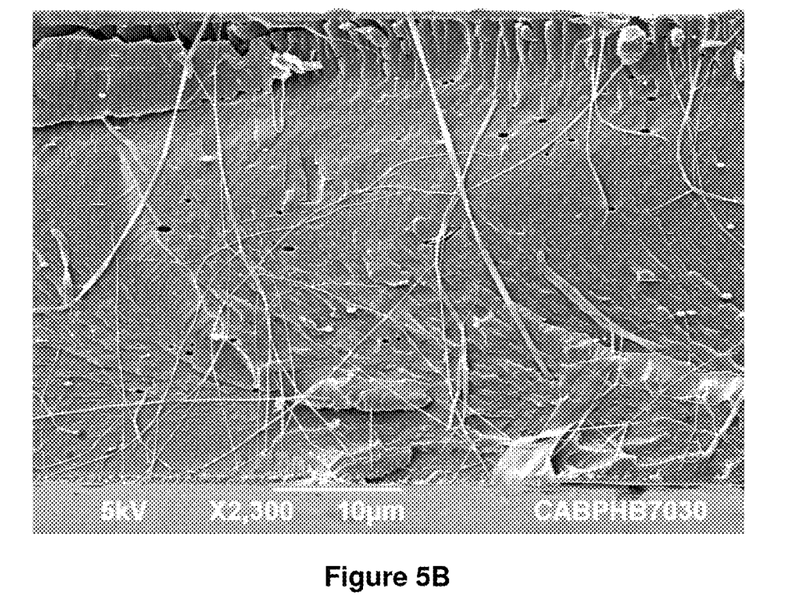
FIG. 5B is a SEM image of a cross-section of the sheet of CAB/PHB blend (70%/30%) film in FIG. 5A, oriented parallel to its CD at 2300× magnification.

FIG. 5B is a SEM image of a cross-section of the sheet of CAB/PHB blend (70%/30%) film in FIG. 5A, oriented parallel to the cross-direction at 2300× magnification. This micrograph shows that the CAB component consistently exhibits brittle fracture while the PHB component occurs as long, mostly sub micron diameter filaments that are often seen to have partially or completely pulled out of the section, leaving a void.

Morphology Analysis: The pure CAB film of FIGS. 2A and 2B shows that the CAB component consistently exhibited a brittle fracture-type morphology. In the blended films, the PHB component occurred as long, mostly sub-micron diameter filaments that are often seen to have partially or completely pulled out of the polymer film matrix. The partial or complete pull-out of the filaments leaves voids, for example, the voids seen in FIG. 4B.

Example Products

The film of this invention as be used as a component film in a number of consumer and industrial products. One example is a personal care absorbent article. The article include the diapers, training pants, feminine pantiliners and pads, adult incontinence pads and pantiliners, adult incontinence pants. The inventive film can be used as an outer cover film in diapers and training pants, or as a baffle film in feminine and adult pads or pantiliners.

Figure 6:
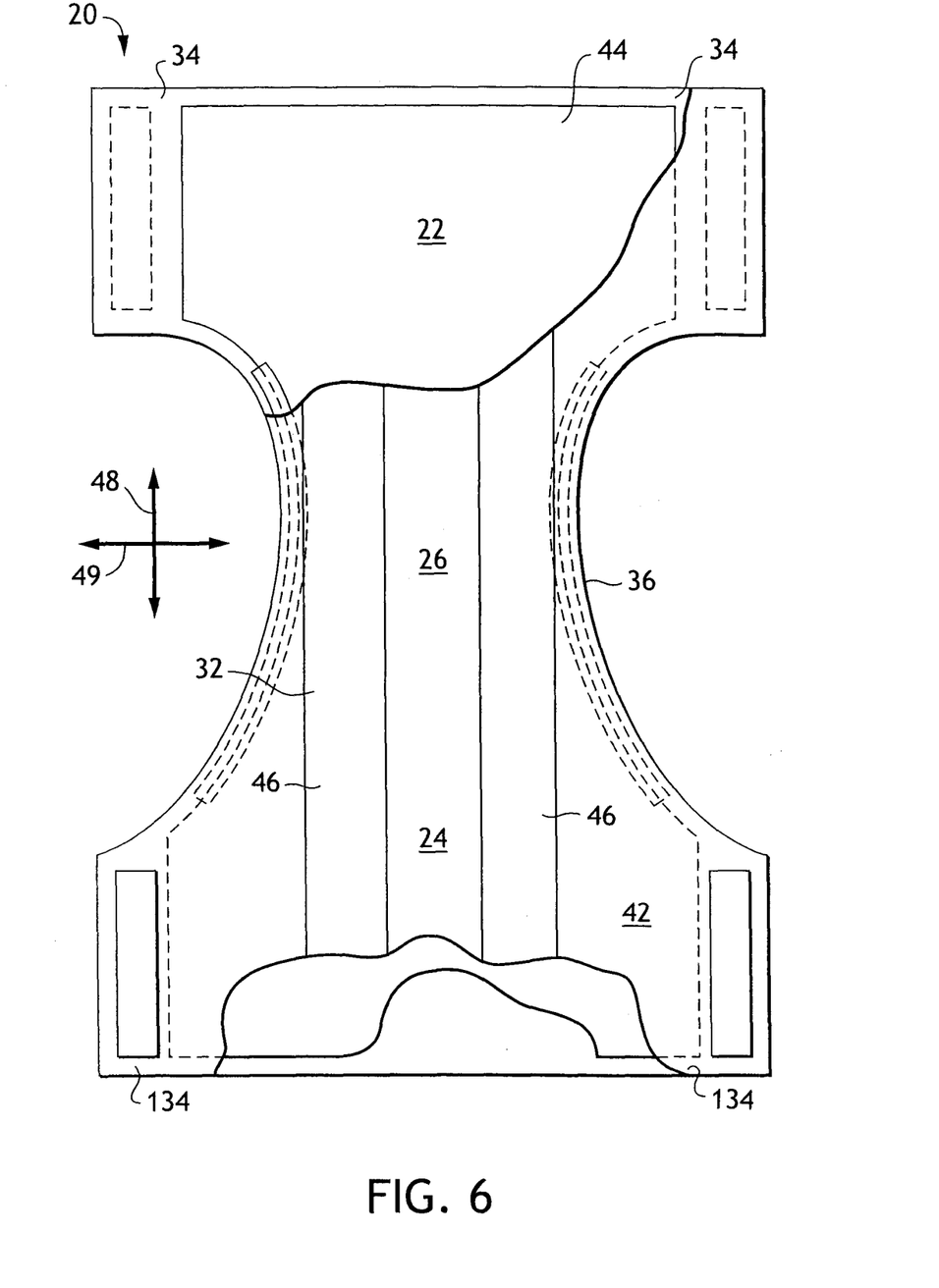
FIG. 6 is a plan view of an absorbent article according to the present invention.
Figure 7:
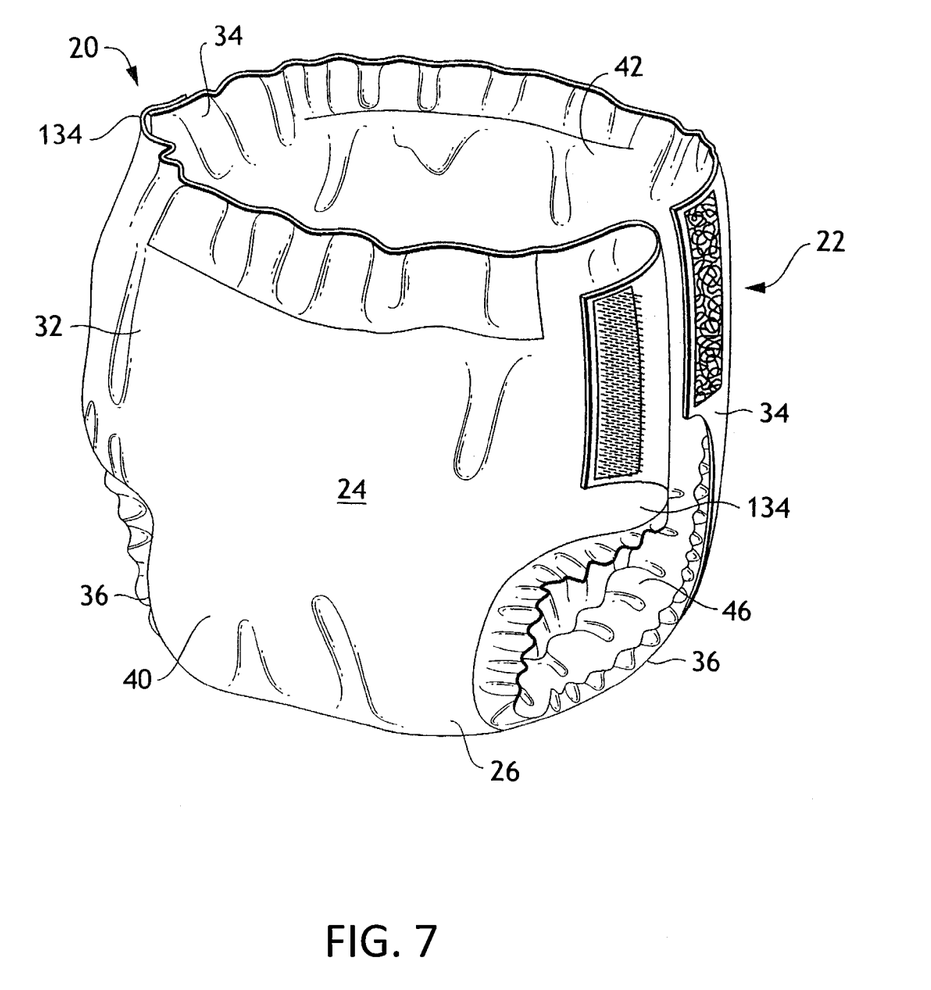
FIG. 7 is a perspective view of the absorbent article of FIG. 6, shown in a partially fastened state.

To gain a better understanding of the present invention, attention is directed to FIG. 6 and FIG. 7 for exemplary purposes showing a training pant of the present invention. It is understood that the present invention is suitable for use with various other absorbent articles, including but not limited to other personal care absorbent articles, health/medical absorbent articles, household/industrial absorbent articles, sports/construction absorbent articles, and the like, without departing from the scope of the present invention.

Various materials and methods for constructing training pants are disclosed in U.S. Pat. No. 6,761,711 to Fletcher et al.; U.S. Pat. No. 4,940,464 to Van Gompel et al.; U.S. Pat. No. 5,766,389 to Brandon et al., and U.S. Pat. No. 6,645,190 to Olson et al., each of which is incorporated herein by reference in a manner that is consistent herewith.

FIG. 7 illustrates a training pant in a partially fastened condition, and FIG. 6 illustrates a training pant in an opened and unfolded state. The training pant defines a longitudinal direction 48 that extends from the front of the training pant when worn to the back of the training pant. Perpendicular to the longitudinal direction 1 is a lateral direction 49.

The pair of training pants defines a front region 22, a back region 24, and a crotch region 26 extending longitudinally between and interconnecting the front and back regions. The pant also defines an inner surface (i.e., body-facing surface) adapted in use (e.g., positioned relative to the other components of the pant) to be disposed toward the wearer, and an outer surface (i.e., garment-facing surface) opposite the inner surface. The training pant has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 134 extending laterally outward at the back region 24.

The chassis 32 includes a backsheet 40 and a topsheet 42 that may be joined to the backsheet 40 in a superimposed relation therewith by adhesives, ultrasonic bonds, thermal bonds or other conventional techniques. The inventive film can be used as backsheet 40 in the illustration. The chassis 32 may further include an absorbent core 44 such as shown in FIG. 2 disposed between the backsheet 40 and the topsheet 42 for absorbing fluid body exudates exuded by the wearer, and may further include a pair of containment flaps 46 secured to the topsheet 42 or the absorbent core 44 for inhibiting the lateral flow of body exudates.

The backsheet 40, the topsheet 42 and the absorbent core 44 may be made from many different materials known to those skilled in the art. All three layers, for instance, may be extensible and/or elastically extensible. Further, the stretch properties of each layer may vary in order to control the overall stretch properties of the product.

The backsheet 40, for instance, may be breathable and/or may be fluid impermeable. The backsheet 40 may be constructed of a single layer, multiple layers, laminates, spunbond fabrics, films, meltblown fabrics, elastic netting, microporous webs or bonded-carded-webs. The backsheet 40, for instance, can be a single layer of a fluid impermeable material, or alternatively can be a multi-layered laminate structure in which at least one of the layers is fluid impermeable. The backsheet 40 can be biaxially extensible and optionally biaxially elastic. Elastic non-woven laminate webs that can be used as the backsheet 40 include a non-woven material joined to one or more gatherable non-woven webs or films. Stretch bonded laminates (SBL) and neck bonded laminates (NBL) are examples of elastomeric composites.

Examples of suitable nonwoven materials are spunbond-meltblown fabrics, spunbond-meltblown-spunbond fabrics, spunbond fabrics, or laminates of such fabrics with films, or other nonwoven webs. Elastomeric materials may include cast or blown films, meltblown fabrics or spunbond fabrics composed of polyethylene, polypropylene, or polyolefin elastomers, as well as combinations thereof. The elastomeric materials may include PEBAX elastomer (available from AtoFina Chemicals, Inc., a business having offices located in Philadelphia, Pa. U.S.A.), HYTREL elastomeric polyester (available from Invista, a business having offices located in Wichita, Kans. U.S.A.), KRATON elastomer (available from Kraton Polymers, a business having offices located in Houston, Tex., U.S.A.), or strands of LYCRA elastomer (available from Invista), or the like, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

One example of a suitable material for a biaxially stretchable backsheet 40 is a breathable elastic film/nonwoven laminate, such as described in U.S. Pat. No. 5,883,028, to Morman et al., incorporated herein by reference in a manner that is consistent herewith. Examples of materials having two-way stretchability and retractability are disclosed in U.S. Pat. No. 5,116,662 to Morman and U.S. Pat. No. 5,114,781 to Morman, each of which is incorporated herein by reference in a manner that is consistent herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The topsheet 42 is suitably compliant, soft-feeling and non-irritating to the wearer's skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from extensible materials such as those described in U.S. Pat. No. 6,552,245 to Roessler et al. which is incorporated herein by reference in a manner that is consistent herewith. The topsheet 42 can also be made from biaxially stretchable materials as described in U.S. Pat. No. 6,969,378 to Vukos et al. which is incorporated herein by reference in a manner that is consistent herewith.

The article 20 can optionally further include a surge management layer which may be located adjacent the absorbent core 44 and attached to various components in the article 20 such as the absorbent core 44 or the topsheet 42 by methods known in the art, such as by using an adhesive. In general, a surge management layer helps to quickly acquire and diffuse surges or gushes of liquid that may be rapidly introduced into the absorbent structure of the article. The surge management layer can temporarily store the liquid prior to releasing it into the storage or retention portions of the absorbent core 44. Examples of suitable surge management layers are described in U.S. Pat. No. 5,486,166 to Bishop et al.; U.S. Pat. No. 5,490,846 to Ellis et al.; and U.S. Pat. No. 5,820,973 to Dodge et al., each of which is incorporated herein by reference in a manner that is consistent herewith.

The article 20 can further comprise an absorbent core 44. The absorbent core 44 may have any of a number of shapes. For example, it may have a 2-dimensional or 3-dimensional configuration, and may be rectangular shaped, triangular shaped, oval shaped, race-track shaped, I-shaped, generally hourglass shaped, T-shaped and the like. It is often suitable for the absorbent core 44 to be narrower in the crotch portion 26 than in the rear 24 or front 22 portion(s). The absorbent core 44 can be attached in an absorbent article, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

The absorbent core 44 can be formed using methods known in the art. While not being limited to the specific method of manufacture, the absorbent core can utilize forming drum systems, for example, see U.S. Pat. No. 4,666,647 to Enloe et al., U.S. Pat. No. 4,761,258 to Enloe, U.S. Pat. No. 6,630,088 to Venturino et al., and U.S. Pat. No. 6,330,735 to Hahn et al., each of which is incorporated herein by reference in a manner that is consistent herewith. Examples of techniques which can introduce a selected quantity of optional superabsorbent particles into a forming chamber are described in U.S. Pat. No. 4,927,582 to Bryson and U.S. Pat. No. 6,416,697 to Venturino et al., each of which is incorporated herein by reference in a manner that is consistent herewith.

In some desirable aspects, the absorbent core includes cellulose fiber and/or synthetic fiber, such as meltblown fiber, for example. Thus, in some aspects, a meltblown process can be utilized, such as to form the absorbent core in a coform line. In some aspects, the absorbent core 44 can have a significant amount of stretchability. For example, the absorbent core 44 can comprise a matrix of fibers which includes an operative amount of elastomeric polymer fibers. Other methods known in the art can include attaching superabsorbent polymer particles to a stretchable film, utilizing a nonwoven substrate having cuts or slits in its structure, and the like.

The absorbent core 44 can additionally or alternatively include absorbent and/or superabsorbent material. Accordingly, the absorbent core 44 can comprise a quantity of superabsorbent material and optionally fluff contained within a matrix of fibers. In some aspects, the total amount of superabsorbent material in the absorbent core 44 can be at least about 10% by weight of the core, such as at least about 30%, or at least about 60% by weight or at least about 90%, or between about 10% and about 98% by weight of the core, or between about 30% to about 90% by weight of the core to provide improved benefits. Optionally, the amount of superabsorbent material can be at least about 95% by weight of the core, such as up to 100% by weight of the core. In other aspects, the amount of absorbent fiber of the present invention in the absorbent core 44 can be at least about 5% by weight of the core, such as at least about 30%, or at least about 50% by weight of the core, or between about 5% and 90%, such as between about 10% and 70% or between 10% and 50% by weight of the core. In still other aspects, the absorbent core 44 can optionally comprise about 35% or less by weight unmodified fluff, such as about 20% or less, or 10% or less by weight unmodified fluff.

It should be understood that the present invention is not restricted to use with superabsorbent material and optionally fluff. In some aspects, the absorbent core 44 may additionally include materials such as surfactants, ion exchange resin particles, moisturizers, emollients, perfumes, fluid modifiers, odor control additives, and the like, and combinations thereof. In addition, the absorbent core 44 can include a foam.

Figure 8A:
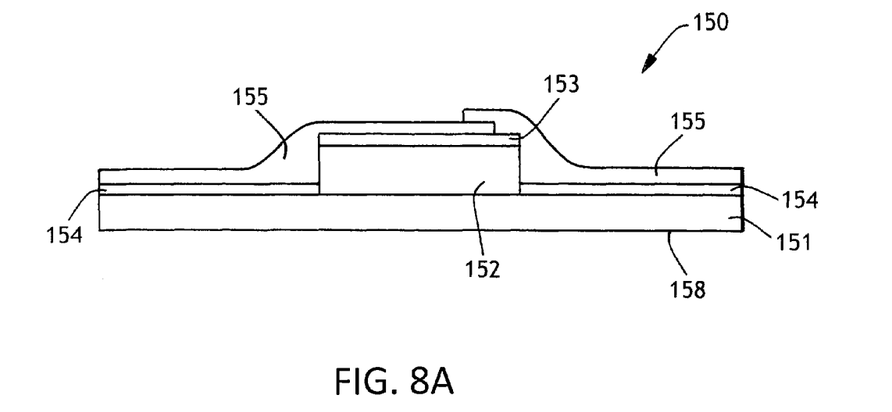
FIG. 8A is a cross-sectional view of another embodiment of an absorbent article of the present invention.
Figure 8B:
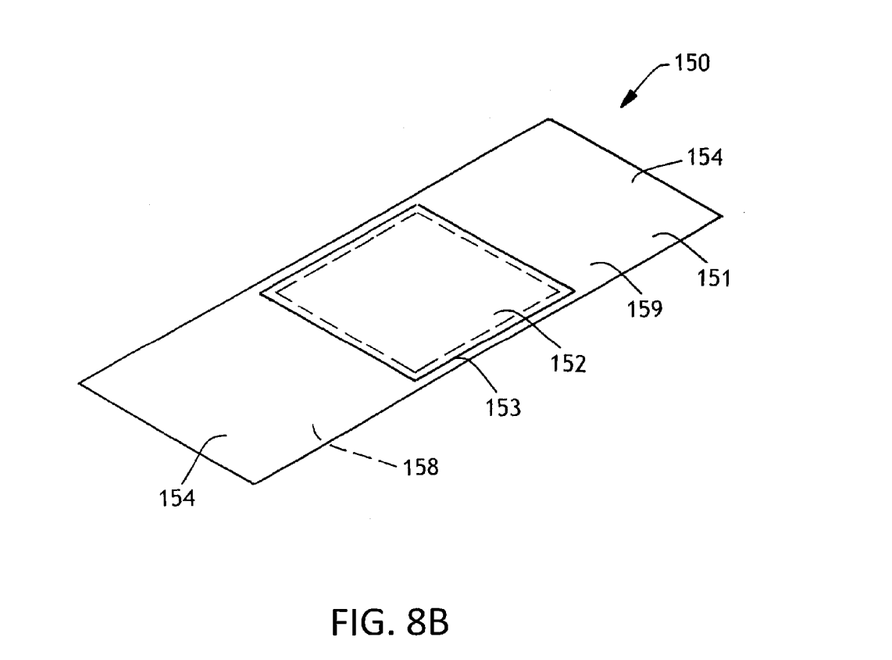
FIG. 8B is a top perspective view of the absorbent article of FIG. 8A.

In addition to the absorbent article described above, the present invention may be exemplified as an absorbent bandage. Attention is directed to FIGS. 8A and 8B, which show a possible configuration for a bandage of the present invention. FIG. 8A shows a cross-section view of the absorbent bandage with optional layers described below. FIG. 8B shows a perspective view of the bandage of the present invention with some of the optional or removable layers not being shown. The absorbent bandage 150 has a strip 151 of material having a body-facing side 159 and a second side 158 which is opposite the body-facing side. The strip is essentially a backsheet and is desirably prepared from the same materials described above for the backsheet. In addition, the strip may be an apertured material, such as an apertured film, or material which is otherwise gas permeable, such as a gas permeable film. The strip 151 supports an absorbent core 152 comprising the superabsorbent polymer composition of the present invention which is attached to the body-facing side 159 of the strip. In addition, an absorbent protective layer 153 may be applied to the absorbent core 152 and can be coextensive with the strip 151. The inventive film can be used as strip 151.

The absorbent bandage 150 of the present invention may also have a pressure sensitive adhesive 154 applied to the body-facing side 159 of the strip 151. Any pressure sensitive adhesive may be used, provided that the pressure sensitive adhesive does not irritate the skin of the user. Suitably, the pressure sensitive adhesive is a conventional pressure sensitive adhesive which is currently used on similar conventional bandages. This pressure sensitive adhesive is desirably not placed on the absorbent core 152 or on the absorbent protective layer 153 in the area of the absorbent core 152. If the absorbent protective layer is coextensive with the strip 151, then the adhesive may be applied to areas of the absorbent protective layer 153 where the absorbent core 152 is not located. By having the pressure sensitive adhesive on the strip 151, the bandage is allowed to be secured to the skin of a user in need of the bandage. To protect the pressure sensitive adhesive and the absorbent, a release strip 155 can be placed on the body-facing side 159 of the bandage. The release liner may be removably secured to the article attachment adhesive and serves to prevent premature contamination of the adhesive before the absorbent article is secured to, for example, the skin. The release liner may be placed on the body-facing side of the bandage in a single piece (not shown) or in multiple pieces, as is shown in FIG. 10A.

In another aspect of the present invention, the absorbent core of the bandage may be placed between a folded strip. If this method is used to form the bandage, the strip is suitably fluid permeable.

Figure 9:
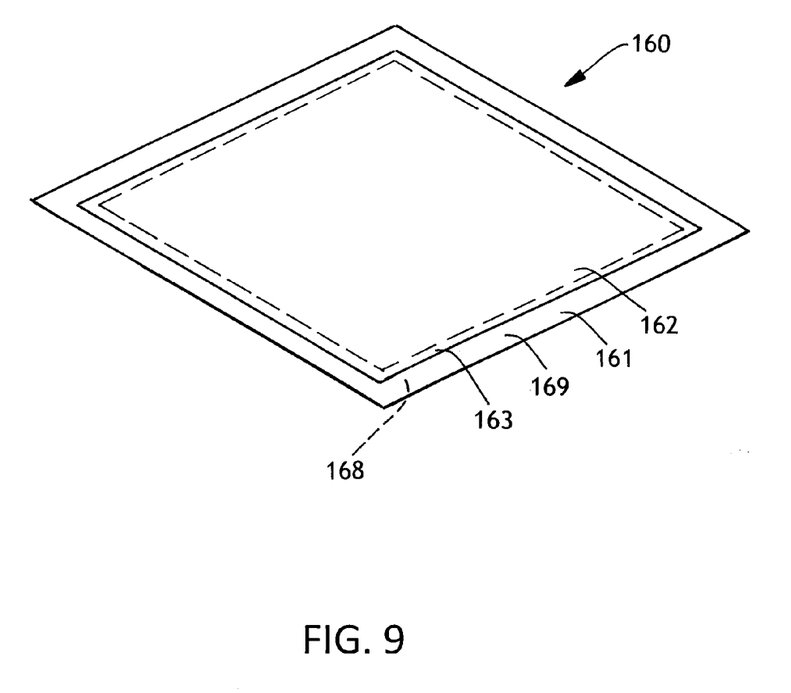
FIG. 9 is a top perspective view of yet another embodiment of an absorbent article of the present invention.

Absorbent furniture and/or bed pads or liners are also included within the present invention. As is shown in FIG. 9, a furniture or bed pad or liner 160 (hereinafter referred to as a "pad") is shown in perspective. The pad 160 has a fluid impermeable backsheet 161 having a furniture-facing side or surface 168 and an upward facing side or surface 169 which is opposite the furniture-facing side or surface 168. The fluid impermeable backsheet 161 supports the absorbent core 162 which comprises the superabsorbent polymer composition of the present invention, and which is attached to the upward facing side 169 of the fluid impermeable backsheet. In addition, an optional absorbent protective layer 163 may be applied to the absorbent core. The optional substrate layer of the absorbent core can be the fluid impermeable layer 161 or the absorbent protective layer 163 of the pad. The inventive film can be used as the backsheet 161 in FIG. 9.

To hold the pad in place, the furniture-facing side 168 of the pad may contain a pressure sensitive adhesive, a high friction coating or other suitable material which will aid in keeping the pad in place during use. The pad of the present invention can be used in a wide variety of applications including placement on chairs, sofas, beds, car seats and the like to absorb any fluid which may come into contact with the pad.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, the film may be used as a packaging film or articles such as product bags, molded containers, bottles, etc. Accordingly, all modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

The invention claimed is:

1. A melt-processed thermoplastic material film comprising:
a blend of about 5 wt. % to about 95 wt. % of a thermoplastic cellulose selected from cellulose ether and cellulose alkanoate with 2 to 10 carbons in an alkanoate group having a melting point temperature between about 100° C. to about 200° C., and about 5 wt. % to about 95 wt. % of a polyhydroxyalkanoate with an average molecular weight of at least 20,000 g/mol.

2. The film according to claim 1, wherein said polyhydroxyalkanoate ranges from about 5 wt. % to about 55 wt. % in the blend.

3. The film according to claim 1, wherein said polyhydroxyalkanoate comprises: poly(3-hydroxy butyrate) (PHB), poly(3-hydroxybutyrate-co-valerate) (PHBV), poly(3-hydroxybutyrate-co-4-hydroxybutyrate) (P3HB-4HB), poly(3-hydroxybutyrate-co-3hydroxyhexanoate) (P3HB-Hx), and/or poly(3-hydroxybutyrate-co-3-hydroxyoctanoate) (P3HB-O).

4. The film according to claim 1, wherein said PHA has a high crystalline content of greater than 55%.

5. The film according to claim 1, wherein said blend also contains one or more plasticizers.

6. The film according to claim 1 wherein the polyhydroxyalkanoate is dispersed into a continuous phase of the thermoplastic cellulose.

7. The film according to claim 1 wherein the thermoplastic material is in the form of a film having a thickness of about 0.5 to about 4.5 mil in both the machine and cross directions.

8. An absorbent article comprising:
a backsheet comprising the film of claim 1;
a topsheet attached to the backsheet, and
an absorbent core disposed between the backsheet and topsheet, and directly attached to either the backsheet or the topsheet.

9. The absorbent article of claim 8 wherein the absorbent article is configured as a training pant, diaper, an adult incontinent garment, a feminine pad, a feminine pantiliner, a bandage or a bed pad.

* * * * *